United States Patent
Nüsser et al.

(10) Patent No.: US 6,742,999 B1
(45) Date of Patent: Jun. 1, 2004

(54) DEVICE FOR DELIVERING SINGLE-PHASE OR MULTIPHASE FLUIDS WITHOUT ALTERING THE PROPERTIES THEREOF

(75) Inventors: Peter Nüsser, Berlin (DE); Johannes Müller, Berlin (DE); Hans-Erhard Peters, Berlin (DE)

(73) Assignees: Berlin Heart AG, Berlin (DE); Forschungszentrum Jülich GmbH, Jülich (DE)

( * ) Notice: Subject to any disclaimer, the term of this patent is extended or adjusted under 35 U.S.C. 154(b) by 0 days.

(21) Appl. No.: 09/959,043

(22) PCT Filed: Apr. 19, 2000

(86) PCT No.: PCT/EP00/03563

§ 371 (c)(1),
(2), (4) Date: Dec. 31, 2001

(87) PCT Pub. No.: WO00/64030

PCT Pub. Date: Oct. 26, 2000

(30) Foreign Application Priority Data

Apr. 20, 1999 (DE) ......................................... 199 18 841

(51) Int. Cl.⁷ ........................... F04B 17/00; F04B 35/04
(52) U.S. Cl. .............................. 417/423.1; 417/423.7; 604/67
(58) Field of Search .......................... 417/423.1, 423.7, 417/423.12, 353–356, 63; 604/131, 151, 9, 67; 600/16, 17

(56) References Cited

U.S. PATENT DOCUMENTS

| | | | | |
|---|---|---|---|---|
| 3,512,851 A | | 5/1970 | Love ........................... 308/10 |
| 3,614,181 A | | 10/1971 | Meeks ......................... 308/10 |
| 3,623,835 A | | 11/1971 | Boyd et al. ................... 73/231 |
| 4,057,369 A | | 11/1977 | Isenberg et al. ............. 417/365 |
| 4,398,773 A | * | 8/1983 | Boden et al. .............. 310/90.5 |
| 4,643,641 A | * | 2/1987 | Clausen et al. ......... 415/170 A |

(List continued on next page.)

FOREIGN PATENT DOCUMENTS

| | | |
|---|---|---|
| EP | 0847767 | 6/1998 |
| EP | 0856666 | 8/1998 |
| GB | 2057590 | 4/1981 |
| WO | WO 97/49440 | 12/1997 |
| WO | WO 98/11650 | 3/1998 |
| WO | WO 98/28543 | 7/1998 |

OTHER PUBLICATIONS

Kawahito et al.: In Phase 1 Ex Vivo Studies of the Baylor/ NASA Axial Flow Venticular Assist Device, in: Heart Replacement Artificial Heart 5, pp. 245–252, Springer Verlag Tokyo 196, Publisher T. Akutso and H. Koyagani.

*Primary Examiner*—Justine R. Yu
*Assistant Examiner*—Han L Liu
(74) *Attorney, Agent, or Firm*—Norris McLaughlin & Marcus, PA

(57) ABSTRACT

A delivery device for a single- or multiphase fluid having a tubular body for axially guiding the fluid, including a motor stator arranged outside the tubular body and a delivery element arranged within the tubular body, comprising a motor rotor. A rotor gap is formed between the delivery element and the hollow body for allowing the fluid to pass through. Mounting arrangements are fixedly disposed in axial direction on each side of the delivery element within the tubular body. Hub gaps are formed between the delivery element and the mounting arrangement. First permanent magnet bearing elements are disposed in the mounting arrangement and second permanent magnet bearing elements are disposed in the delivery element. The first and the second permanent magnet bearing elements functionally work together and are magnetized in axial direction and have opposite polarity. Position sensors associated with each of the first permanent magnet bearing elements and a stabilizer is disposed around the hollow body.

13 Claims, 6 Drawing Sheets

U.S. PATENT DOCUMENTS

| | | | |
|---|---|---|---|
| 4,688,998 A | 8/1987 | Olsen et al. | 417/356 |
| 4,763,032 A * | 8/1988 | Bramm et al. | 310/90.5 |
| 4,779,614 A * | 10/1988 | Moise | 600/16 |
| 4,812,694 A | 3/1989 | Fremery | 310/905 |
| 4,948,348 A | 8/1990 | Doll et al. | 417/365 |
| 4,957,504 A | 9/1990 | Chardack | 623/3 |
| 5,112,200 A | 5/1992 | Isaacson et al. | 417/356 |
| 5,126,610 A | 6/1992 | Fremerey | 310/90.5 |
| 5,180,287 A * | 1/1993 | Natwick et al. | 417/43 |
| 5,211,546 A * | 5/1993 | Isaacson et al. | 417/356 |
| 5,385,581 A | 1/1995 | Bramm et al. | 623/3 |
| 5,635,784 A | 6/1997 | Seale | 310/90.5 |
| 5,695,471 A | 12/1997 | Wampler | 604/131 |
| 5,947,892 A | 9/1999 | Benkowski et al. | 600/16 |
| 6,015,272 A * | 1/2000 | Antaki et al. | 417/356 |
| 6,053,705 A | 4/2000 | Schöb et al. | 417/53 |
| 6,092,994 A | 7/2000 | Yamamoto et al. | 417/53 |
| 6,201,329 B1 * | 3/2001 | Chen | 310/90.5 |
| 6,527,699 B1 * | 3/2003 | Goldowsky | 600/16 |

* cited by examiner

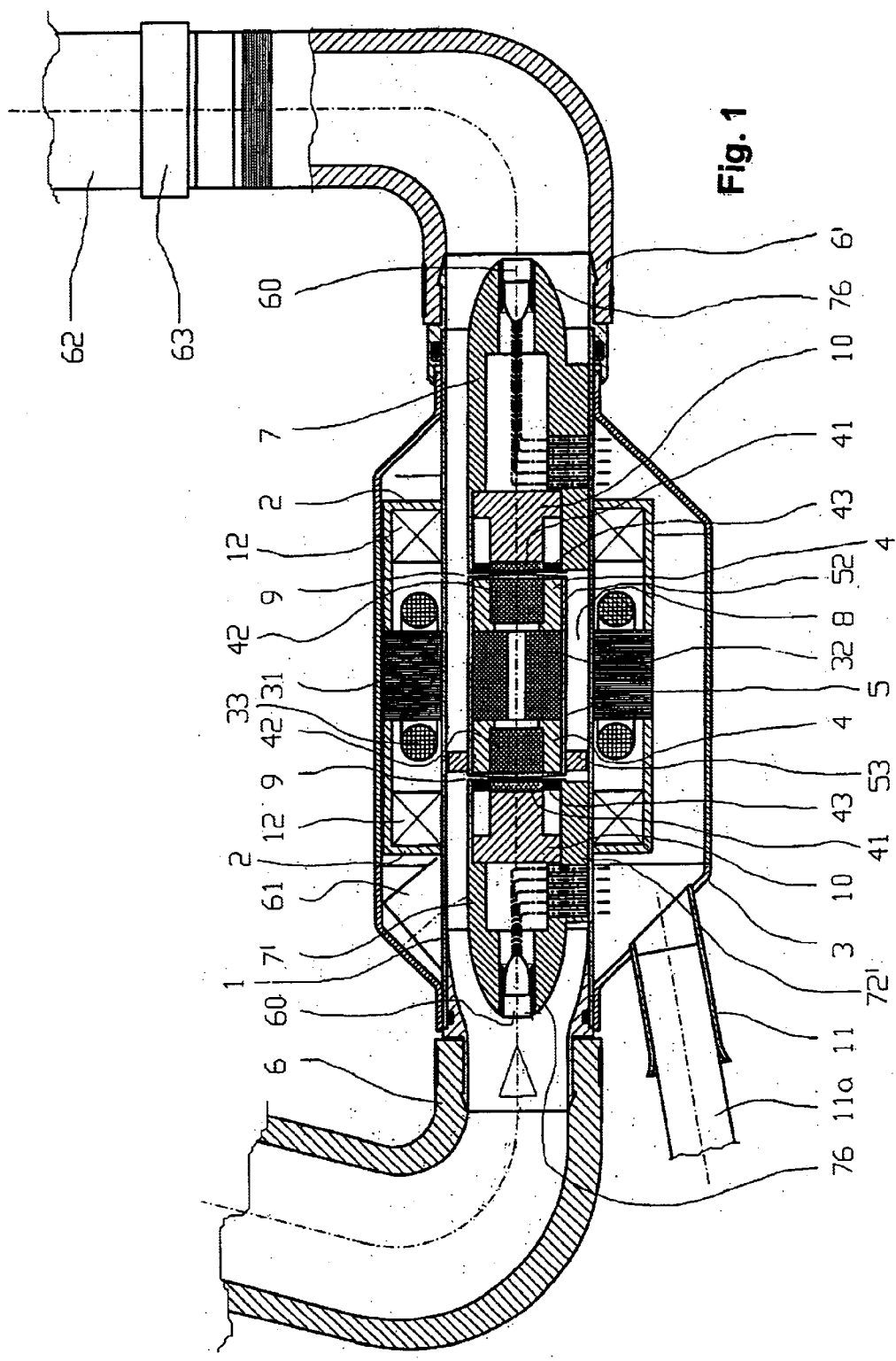

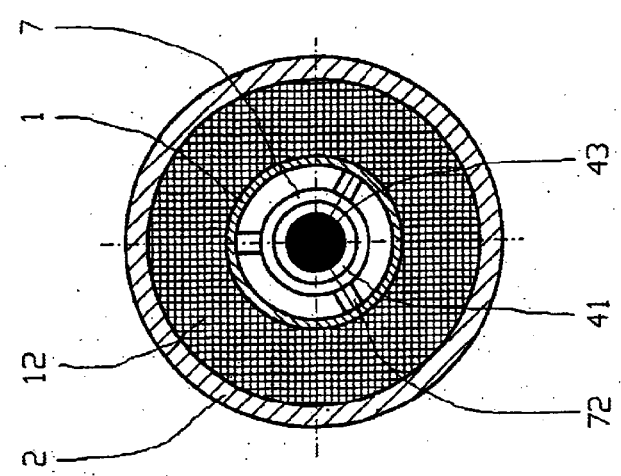
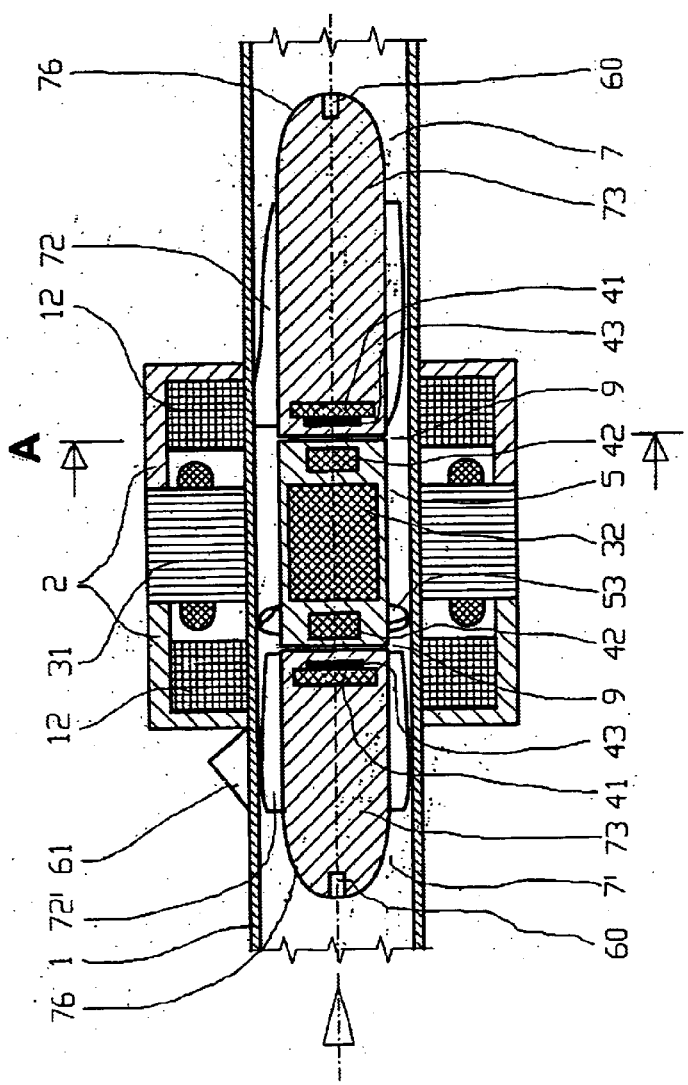
Fig. 2a
Cross-section A-A
Fig. 2

Cross-section A-A

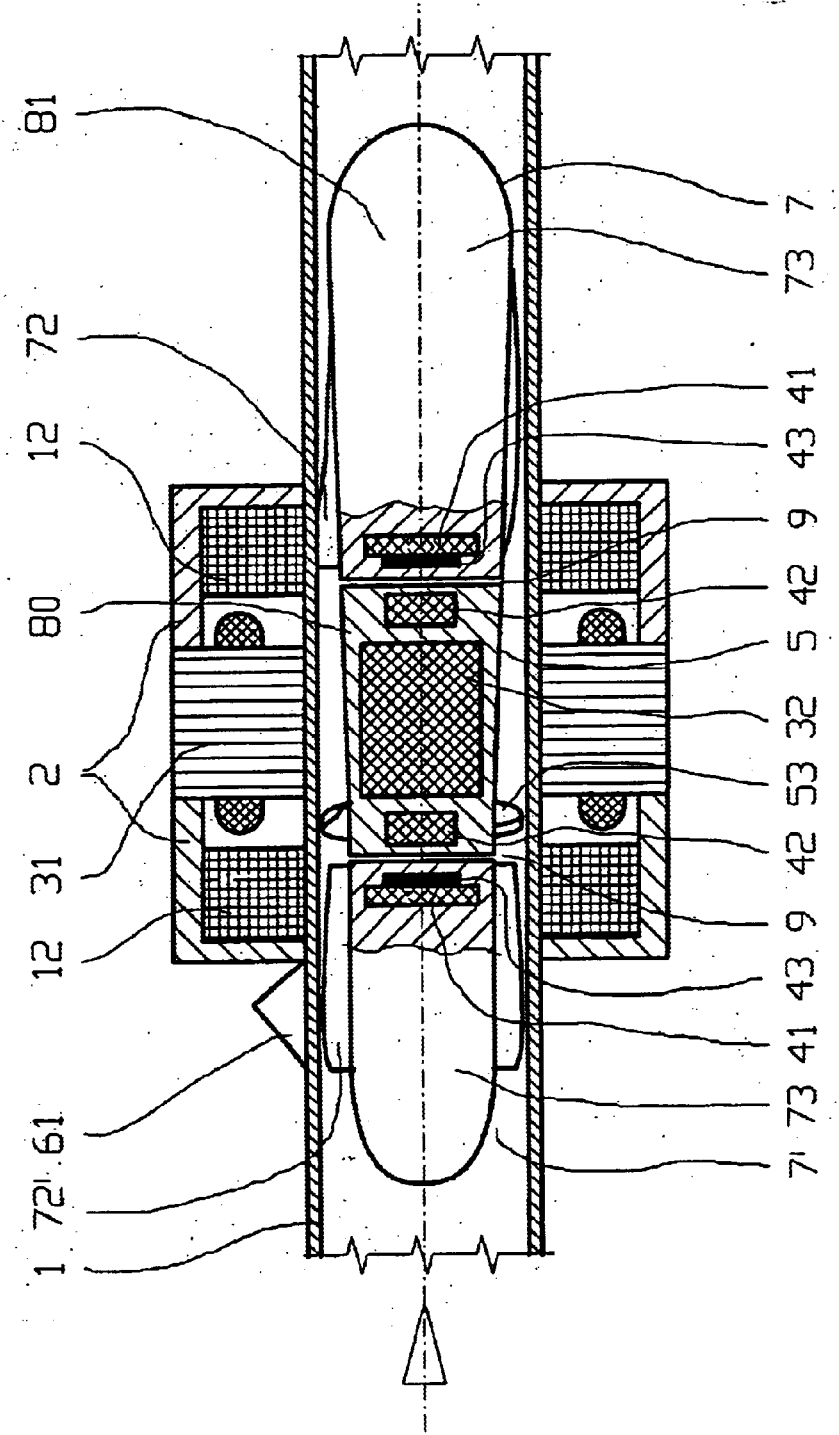

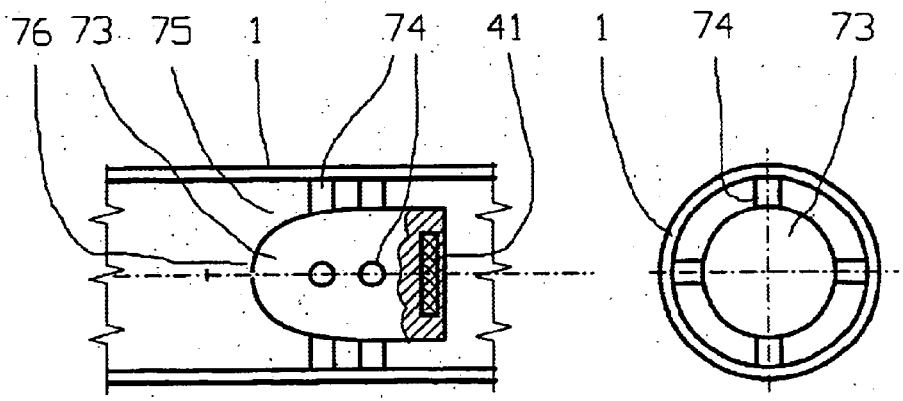
Fig. 3a  Fig. 3b
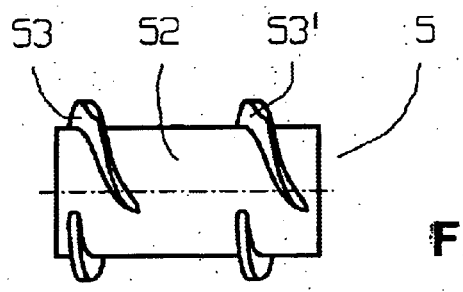
Fig. 4
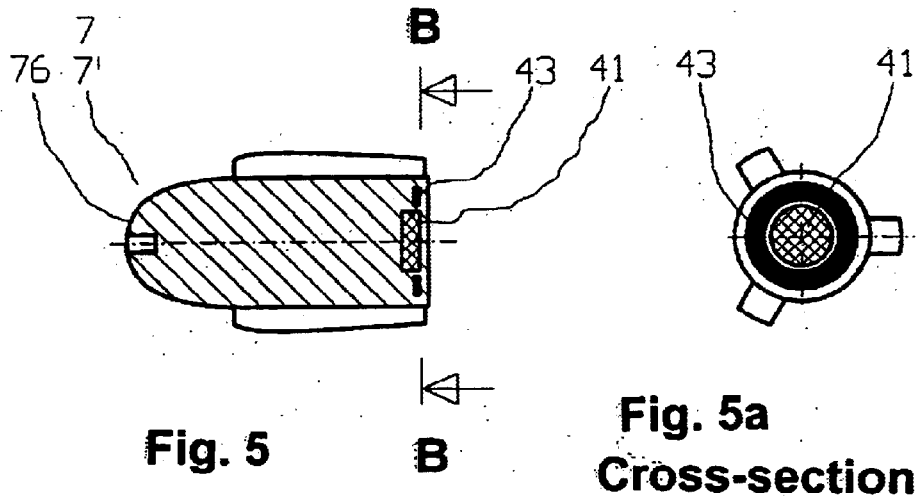
Fig. 5
B
Fig. 5a
Cross-section B-B

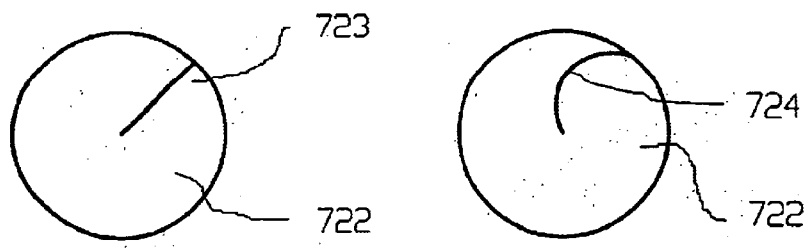
Fig. 6a    Fig. 6b
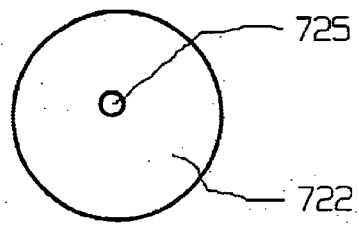
Fig. 6c
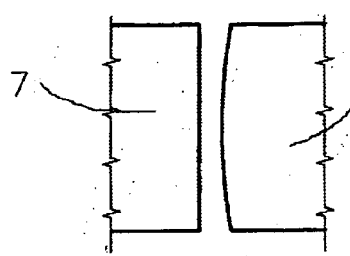 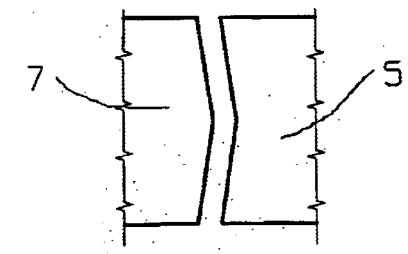
Fig. 7    Fig. 7a
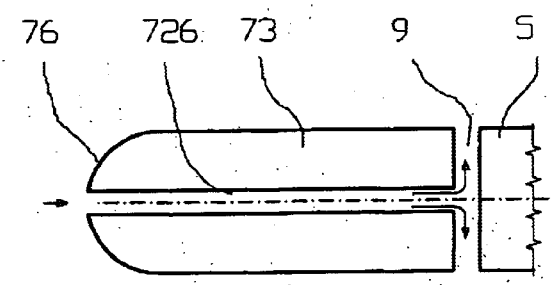
Fig. 8

DEVICE FOR DELIVERING SINGLE-PHASE OR MULTIPHASE FLUIDS WITHOUT ALTERING THE PROPERTIES THEREOF

BACKGROUND OF THE INVENTION

The invention relates to a device for delivering single-phase or multiphase fluids without altering the properties thereof.

Especially less stable multiphase fluids, for example emulsions and dispersions, which can experience irreversible changes by an energy insertion, can disadvantageously get during the delivery in corresponding devices, like pumps, into instable areas.

A very sensitive fluid system is blood. This opaque red body liquid of vertebrate animals circulates in a closed vascular system, wherein the rhythmical contraction of the heart presses the blood into the different areas of the organism. In this case the blood transports the respiratory gases, which are oxygen and carbon dioxide, as well as nutrients, metabolic products and body own substances. In this case, the blood vascular system including the heart is hermetically sealed from the environment, so that the blood experiences no changes in the healthy organism, when it is pumped via the heart through the body.

It is known, that the blood tends, when contacting with materials foreign to the body or through foreign energy affect, to a haemolysis and a thrombi formation. The formation of thrombi can be deadly for the organism, as they lead to a clogging up in the far branched vascular system. Haemolysis describes the condition, that the red blood cells are lysed destroyed further than the physiological degree. The causes for the haemolysis could be mechanical or metabolical. Increased haemolysis causes multiple organ damage and can lead to the death of the human being.

On the other hand it has been shown, that it is principally possible to support the pump capacity of the heart under specific constructive conditions or even to replace the natural heart by an artificial heart, but a constant operation of implanted heart support pumps or artificial hearts is at the moment only limitedly possible, as the interaction of these artificial products with the blood still lead to disadvantageous changes of the blood.

In the known State of the Art different development directions of blood pumps are distinguishable. Heart support pumps and artificial hearts can be designed starting from the required pressure difference and the volume flow, as well as the displacement principal as a so-called pulsating pump or according to the turbo principle as a radial or axial flow device. At the moment these three named designs are developed in parallel. The flow devices show because of the high capacity density of this type of devices smaller dimensions than piston devices. Within the group of pumps, which function according to the turbo principal, the axial pump variant is as a rule smaller than the radial variant. A turbo device can be designed generally for the given pressure difference and the given volume flow very differently, for example as an axial or a radial pump with greatly different rotational speeds.

The axial blood pumps known from the State of the Art, comprise generally an outer cylindrical pipe, in which a delivery element rotates, which is formed as a rotor of a motor stator arranged outside and which, therefore, transports the blood in an axial direction. The support of the delivery element is a problem. A purely mechanical support is disadvantageous because of the damage of the blood and even because of the relatively high friction values. Also the up-to-now described magnet bearing types have not lead to a satisfactory solution.

From Kawahito et al.: In Phase 1 Ex Vivo Studies of the Baylor/NASA Axial Flow Ventricular Assist Device, in: Heart Replacement Artificial Heart 5, pages 245–252, Springer Verlag Tokyo 1996, Publisher T. Akutso and H. Koyagani, an axial blood pump according to the state of the art for the support of an ill heart is known, which can be implanted into the chest area of a patient. The axial blood pump has a rotating impeller with a blading, which is supported within a blood carrying pipe and is driven by means of an electric motor.

For this the impeller is formed as a rotor of the electric motor and is coupled by means of magnets mounted on the blading with the stator of the electric motor fast with the housing. An axial and a radial support of the rotor takes place via a toe bearing , in which the rotor is supported point-by-point on bearing elements arranged in the flow. Such an arrangement is also known from U.S. Pat. No. 4,957,504.

The known blood pump has the disadvantage, that the to be delivered blood experiences in a considerable extent a traumatisation and damage. In this case the danger lies generally in the formation of thrombi. The reason for this lies essentially in the formation of wake areas of the bearings.

A further disadvantage is undoubtedly the limited endurance of the mechanical bearing because of wear.

U.S. Pat. No. 4,779,614 discloses an implantable axial blood pump, which consists of an outer cylindrical pipe and a rotor hub rotating in this pipe for the blood delivery. The rotor is magnetically supported and carries at the same time the rotor magnets of the drive and the impeller blades. The magnetically supported rotor forms with the stator blading mounted on the outer pipe long, narrow gaps. The arrangement of two motor-stator-combinations respectively on the ends of the pump shall stabilize the positioning of the rotor. The positioning in the direction of the axis is stabilized by another pair of magnets, which shall take up the axial forces of the rotor as well. Although a relatively wide annular gap for the fluid flow is provided and with the magnetic bearing of the rotor important development goals for the implantable blood pump concerning a compact design and free from sealing and support problems can be aimed at, the blood pump has great disadvantages concerning the function and the structural design of the pump. The exceptionally long narrow gaps between the rotor hub and the stator blades on the stator increase the danger of a blood damage by high velocity gradient of the gap flows. The arrangement of two motors required for the rotor stabilization is designwise cumbersome. Furthermore, the rotor is not form-fittingly secured in the axial direction and is therefore a residual risk.

The U.S. Pat. No. 5,385,581 also discloses an axial blood pump with magnet bearing. The bearing magnets arranged in the rotor and in the stator area are charged with an opposing polarity.

Disadvantageously this leads to the breakdown of the pump, when the bearing fails. Furthermore, it is disadvantageous that no so-called post guide lattice is provided, i.e. the total pressure is produced by the impeller, and the residual spin energy remains in the flow.

A further axial blood pump with magnetic bearing is known from WO97/49 440. The magnetic bearing is carried out at the conically formed rotor ends of the rotor, which forms the impeller. The fixedly arranged pole shoes are arranged opposite to the rotor ends, which pole shoes guide the flow of the permanent magnets. The bearing necessitates an active stabilization with at least four stabilization coils in axial as well as in radial direction. In a further variant the bearings with radially magnetized permanent magnet rings with changing magnetization direction are proposed, which are indeed difficult to control.

From WO 98/11 650 a further axial blood pump with a so-called bearingless motor is known. The "bearingless" motor is a combination of a motor and a magnetic bearing. The position of the rotor is stabilized passively by permanent magnets with reference to three degrees of freedom translation in the x-direction, tipping in the x- and y-direction. The passive stabilization is achieved by a permanent magnetic rotor ring, which is surrounded on the stator side by a soft iron ring. Control and driving coils, which are connected to the soft iron ring, allow a drive with reference to three degrees of freedom. The low bearing stiffness requires additional measures. Furthermore, a bearing stabilization is necessary in the x- and y-direction, which leads to a great extent of measuring technology to be applied and can result in a high heating of the pump because of the active coils.

For the delivery of chemical fluids an axial propeller pump is known from EP-A 0 856 666. The delivery element is magnetically supported between two mounting elements, which are attached in a tubular hollow body with the retention of an annular gap. The delivery element forms the rotor of a motor, which stator is arranged externally of the tubular hollow body. The magnetic bearing is achieved in the radial direction by radial magnetized permanent magnets and in the axial direction by means of electromagnetic coils, which as far as possible are decoupled from these. Radially magnetized permanent magnets necessitate a defined minimum size and small air gaps.

Therefore, the delivery gap can only be very small, which in the here present delivery task (propeller pumps produce a high pressure at a small delivery volume) which is not a hindrance for other pumps, but, however, is especially not acceptable for blood pumps.

Furthermore, the complete axial rigidity, which is very high compared to the radial rigidity because of the delivery pressure of the to be delivery medium, has to be exerted by the stabilization coils, which requires a specific current value, which leads to a corresponding energy demand and to heating. The control of the axial position slows down with increasing current value, so that the pump is only suitable for pulsating delivery tasks to a limited extent.

It is the object of the invention to provide a device for the gentle delivery of single or multiphase fluids of a simple structural design, which does not or only inconsiderably change the to be delivered fluid in its characteristics, in which wake areas and vortexing of the to be delivered fluid are minimized and a pulsating delivery is enabled.

The object is solved according to the characterizing features of claim 1.

Preferred and advantageous embodiments of the invention are given in the sub-claims.

According to this the delivery element is supported free of contact between the mounting elements, respectively separated to each by a hub gap, by means of permanent magnetic bearing elements, which are arranged in the mounting elements as well as in the delivery element, which functionally work together and which magnetic acting faces are opposed to each other and are magnetized in the axial direction and poled oppositely. Sensors for the positional detection and stabilizers for the positional correction are arranged in the mounting elements and on or in the wall of the hollow body.

The device according to the invention achieves a simple design. The permanent magnetic bearing elements necessary for the magnetic bearing, are additionally arranged to the permanent magnetic elements of the motor rotor directly on the delivery element. The magnetic bearing takes up advantageously the axial as well as the radial forces. The axial stabilization offers an active control of the axial position of the delivery element, wherein annular coils, arranged on the front face of the delivery element, produce an axial magnetic flow, which superimposes the axial magnetic flow of the permanent magnetic bearing elements and serves for the control of the axial position.

The rotor gap, which has to be provided between the external face of the delivery element and the inner face of the tubular hollow body, has to be designed in such a way, mat the motor losses as well as the flow losses generated by the gap are minimized Hereby it is important, that the generated motor losses are increasing the flier away the motor rotor is arranged from the motor stator. A smaller rotor gap on the side of the motor is to be seen as advantageous. On the other hand a smaller rotor gap leads, however, to larger friction losses of the flow and therefore, is technologically disadvantageous concerning the flow. A suitable compromise for blood pumps lies for example in the named rotor gap width of 0.5 to 2.5 mm.

An advantageous embodiment of the invention consists in that further sensors for the determination of the instantaneous blood volume flow and for the instantaneous pressure difference generated by the pump are integrated in the hubs of the axial blood pump and/or in the walls of the tubular hollow body. Both measuring values are present in the controller of the delivery device for the variance comparison and therewith opens the possibility for a control of the delivery process in the sense of a physiological optimal pulsating delivery, adapted to the natural heart action by means of a time dependent rotational speed change of the rotor or of a pulsating pump optimized in the sense of a lower energy consumption and also realised by a time dependent rotational speed change.

In a preferred way the mounting elements are formed as fluid guide units with fluid blades. Because of this flow losses are minimized.

In a further advantageous embodiment of the invention means are provided on the front face of the rotor hub, which deliver radially the fluid present in the hub gap between the fluid guide unit and the delivery element to the outside, for example radial blades, grooves, bulgings or convex formations.

A further advantageous embodiment of the invention consists in that an axially extending bore is provided in at least one of the fluid guide units, through which the to be delivered fluid passes, and which serves, that fluid present in the hub gap between the fluid guide unit and the delivery element is transported radially to the outside.

Both prementioned embodiments influence the radial pressure distribution and produce compensation flows for the prevention of dead water areas in the hub gap between the front faces of the fluid guide unit and the delivery element.

In a further embodiment of the invention the delivery element, especially the rotor hub, has two blades distanced in the axial direction. Herewith a so-called tandem grid is formed. The pressure increase to be produced by each blading row is advantageously reduced. Furthermore, this special arrangement of the rotor of the delivery device limits additionally the disturbing tipping movement of the same.

BRIEF DESCRIPTION OF THE DRAWINGS

Following the invention is described in detail by means of an example with reference to the figures.

FIG. 1 shows a sectional view of an axial blood pump;

FIG. 2 shows a longitudinal sectional view of an axial delivery device with a magnet bearing, axial stabilization and positioning sensory mechanism;

FIG. 2a shows a sectional view of the axial delivery device along the line A—A of FIG. 2;

FIG. 2d shows a longitudinal sectional view of an axial delivery device with a conical delivery element;

FIG. 3a shows a magnetic mounting for an axial delivery device;

FIG. 3b shows a cross sectional view of the magnetic mounting of FIG. 3a;

FIG. 4 shows a delivery element with double blading;

FIG. 5 shows a fluid guide unit with positioning sensor and permanent magnet bearing element;

FIG. 5a shows a sectional view of the fluid guide unit along the line B—B of FIG. 5;

FIG. 6a shows a schematical front view of the front face of a rotor hub or hub;

FIG. 6b shows a schematical front view of the front face of a further rotor hub or hub;

FIG. 6c shows a schematical front view of the front face of a rotor hub or hub with an eccentric projection;

FIG. 7 shows a schematical sectional view of a hub gap, formed between delivery element and hub of a mounting element;

FIG. 7a shows a schematical sectional view of a hub gap, formed between delivery element and hub of a mounting element; and FIG. 8 shows a schematical sectional view through a hub with an axial bore.

DETAILED DESCRIPTION OF THE PREFERRED EMBODIMENTS

Figure 2C:
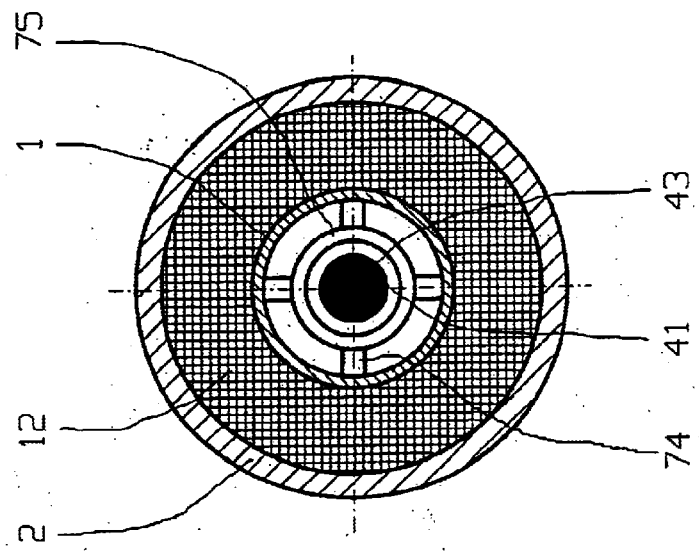
FIG. 2c shows a sectional view of the axial delivery device along the line A—A of FIG. 2b.

FIG. 1 shows an examplanary embodiment of a blood pump according to the invention having a pump housing 3 and a stabilizer housing 2. A motor stator 31 with a motor winding 33 is arranged outside and around a tubular hollow body 1, in which in axial direction the fluid is delivered. The motor stator 31 drives a delivery element 5, comprising a motor rotor 32 and a rotor hub 52 and which is supported inside the tubular hollow body 1. The rotor hub 52 has a rotor blading 53. In the flow direction, in front of and behind the rotor hub fluid guide units 7, 7' with fluid guide blading 72, 72' are mounted on the inner wall of the tubular hollow body 1. Between the fluid guide units 7, 7' and the rotor hub 52 a so-called hub gap 9 is formed. The motor rotor 32 combined with the rotor hub 52, can be rotated via the motor stator 31.

During the operation of the blood pump the discharged blood is carried through an elbow 6 to the delivery element 5 and there is rotated by means of the rotor blading 53, wherein the rotor hub 52 serves for producing advantageous flow dynamical conditions. A flow technical advantageous flow against the rotor blading 53 is provided by the fluid guide unit 7' with its blading 72' rigidly connected upstream of the hollow body 1. The pressure sensor 60 allows a pressure measuring in the inflowing fluid. The delivery element 5 is in the known way driven by magnetic coupling of the motor rotor 32 with the motor stator 31. A forming of thrombi in blood as the delivered medium is greatly minimized, as no bearing elements are arranged in the flow, which could cause wake areas, because of the magnetic bearing. A vortexing and therewith connected flow losses only appear in a small extent. A rotor gap 8 between the rotor hub 52 and the inner wall of the hollow body 1 has in this case a width, which keeps the flow losses small and at the same time also limits the motor losses, which increase with increasing distance of the motor rotor 32 to the motor stator 31. A width of the rotor gap 8 of between 0.5 to 2.5 mm has shown to be especially advantageous. After the acceleration of the fluids by the rotor blading 53 of the rotor hub 52 and a therewith connected pressure build-up, the fluid is guided into the fluid guide unit 7, where it experiences a deflection in the axial direction and further a pressure increase is carried out. Because of the design of the fluid guide blading 72 of the fluid guide unit 7 it is secured, that the deflection of the fluid in the axial direction is carried out gently and also essentially without vortexing.

The blood leaves the blood pump via the elbow 6' and flows into an aortic cannula 62, which is attached by means of a releasable connection element 63 on the elbow. A specially shielded cable 11a, comprising the supply and signal lines for the motor stator 31, the axial stabilizer 12 and the sensory mechanism 60, 61 and 43, is connected via the cable muff 11 with the blood pump.

The function of the magnetic bearing is described by means of FIGS. 2 and 2a.

FIG. 2 and FIG. 2a show, furthermore, in the longitudinal sectional view and in the sectional view, respectively, a further embodiment of a blood pump having a magnetically supported rotor hub 52. In the rotor hub 52 the motor rotor 32 is integrated, having permanent bearing elements 42 arranged at its ends, which are supported in a mounting 4. In the fluid guide units 7, 7' permanent magnet bearing elements 41 are arranged directly opposite permanent magnet bearing elements 42. In this case the permanent magnet bearing elements 41 and 42 are charged with an opposed polarity. The axially directed attraction force arising between the permanent magnet bearing elements 41, 42 ensures that the delivery element 5 is held coaxially in the tubular hollow body 1 and that radial deflections are correlated. Positioning sensors 43 also arranged in the fluid guide units 7 and 7', determine the width of the hub gap 9 and measure and control this gap by means of the axial stabilizer 12. The axial stabilizer 12 is arranged in a stabilizer housing 2. The axial stabilizers 12, formed as windings, produce when the current supply is switched on, a magnetic field, which is transmitted via the stabilizer housing 2 and the flow guide elements 10 in such a way, that the delivery element 5 takes up a stable axial position between the fluid guide units 7 and 7'. At the ends of the fluid guide units 7 and 7', as well as on the outer wall of the tubular hollow body 1, pressure sensors 60, as well as a flow sensor 61 for the characterization of the flow are attached. The delivery element 5 comprised of the motor rotor 32 and the permanent magnet bearing elements 42, as well as of the rotor blading 53, is rotated by means of the motor stator 31. Radial variations during the rotation are levelled-out by the opposingly charged permanent magnet bearing elements, while the axial stabilization is carried out via the positioning sensors 43 and the axial stabilizers 12. The concentration of the main mass of the permanent magnet bearing elements 42 in the area of the axle of the delivery element 5 makes it possible to drive the pump in a pulsation operation, e.g. by a fast change of rotational speed of the rotor.

The permanent magnet bearing elements 41 and 42 are alternatively formed as permanent magnet rings also having an axial magnetization instead of as a solid cylinder. Any embodiments, known to the specialist, can be used for the exact design of the permanent magnet bearing elements 41 and 42.

For stabilization of the axial positioning of the delivery element 5 and of the rotor hub, respectively, an arial stabilizer 12 is provided in the embodiment as an example, which interacts with positioning sensors 43 and which acts via the fluid guide units 7 and 7' on the end faces of the delivery element 5, respectively, and uses an electronic control circuit, not represented in this case. The axial stabilizer 12 causes an active control of the axial positioning of the delivery element 5, wherein the stabilizer windings are acted upon by currents according to the carried out control and causes at the same time a magnetic flow, which overlays the axial magnetic flow of the permanent magnet elements and serves for the control of the axial positioning. The positioning sensors 43 determine variations from the desired axial position of the delivery element 4 and transmit this information to the control circuit.

Figure 2B:
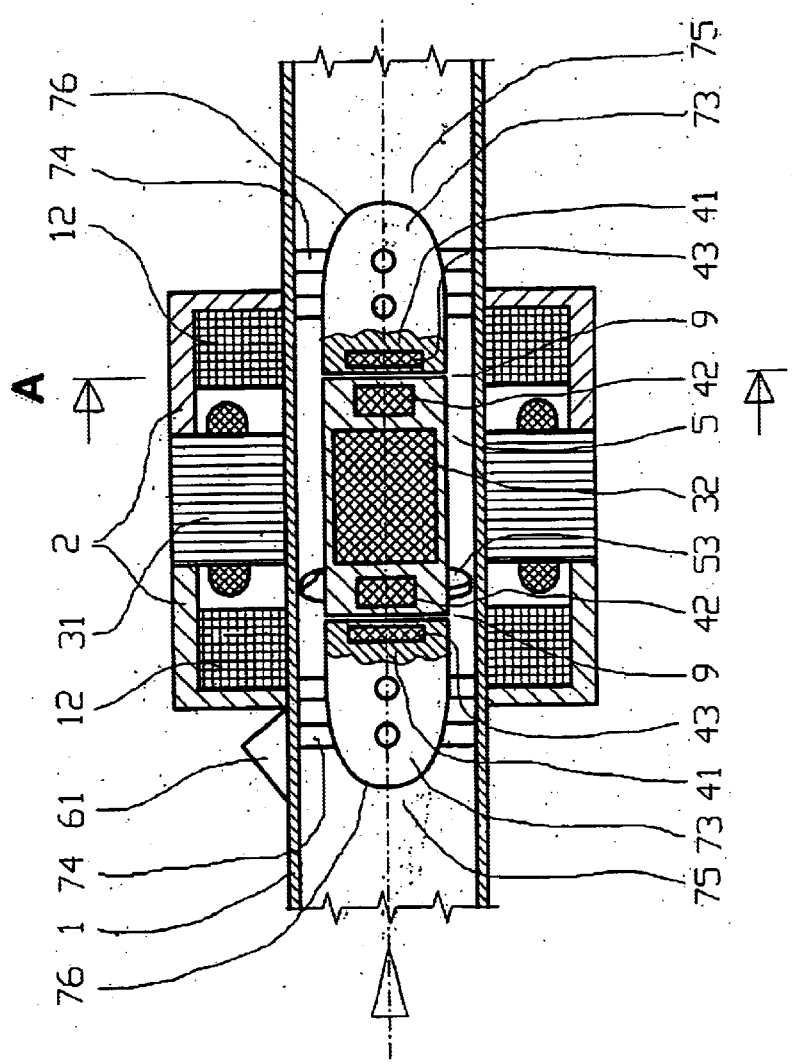
FIG. 2b shows a longitudinal sectional view of an axial delivery device with magnetic mounting.

FIG. 2b and FIG. 2c show a longitudinal sectional view and a sectional view of a further embodiment of a device according to the invention. The mountings 75 provided in front of and behind the delivery element 5 viewed in the flow direction, consist of a hub 73, mounted with supports 74 on the inner wall of the tubular hollow body 1. The supports 74 are arranged here for example around the hub 73 at a distance of 90°. In general one support 74 would also be sufficient. The mounting 75 serves essentially for receiving the permanent magnet bearing elements 41. The opposed permanent magnet bearing elements 41 and 42 are also charged with opposing polarity, in this case. For the axial stabilization the axial stabilizer 12, the positioning sensor 43 and a control electronic, not represented, are used.

In a further embodiment of FIG. 2d the delivery element 5 and the fluid guide unit 7 are formed conical. A conical rotor 80 of the delivery element 5 expands in flow direction and merges, further conically expanding, in a conical guide unit 81. The permanent magnet bearing elements 41 and 42 are charged with opposing polarity. The axial stabilization is also carried out via the positioning sensors 43 in connection with the axial stabilizer 12.

FIGS. 3a and 3b show, respectively, a longitudinal sectional view and a sectional view in detail an examplanary embodiment of the mounting 75 with supports 74.

FIG. 4 shows a delivery element 5 with the rotor hub 52 arranged around the two rotor bladings 53 and 53'. The arrangement of two or more rotor bladings 53 makes it possible, to increase the effect of the blading of the delivery element 5.

FIG. 5 and FIG. 5a show a longitudinal section view and a sectional view, respectively, of the fluid guide units 7 or 7', respectively, in which the permanent magnet bearing element 41 is surrounded by the positioning sensor 43.

Measures, which influence the radial pressure distribution and generate compensation flows for the prevention of dead water areas in the area of the rotor hub 52, i.e. in the hub gap 7 between the front faces of the fluid guide unit 7 and 7' and of the delivery element 5, are shown in FIGS. 6a, b, c, 7 and 7a. According to FIG. 6a a rib 723 extending radially to the outside from the center, is arranged on a front face 722 of the fluid guide unit 7, 7'. According to FIG. 6b the rib 724 is formed curve-like. Instead of such ribs also convex and/or concave projections, radial bladings, micro-bladings, ribs, recesses and eccentric projections 725 (FIG. 6c) of any form on the front face 722 or even simply a roughness of the upper face can be provided. Important is only, that these are means, by which the fluid can be delivered out off the hub gap 9 (compare FIG. 8) at rotation of the delivery element 5. These means can, of course, also be arranged on the front face of the rotor hub 52.

The representation according to FIG. 7 causes advantageously additionally an improvement of the resistance to galling in case of failing of the axial stabilization.

In FIG. 8 the hub 73 has an axial bore 726, through which the to be delivered fluid flows and which causes, that the fluid remaining in the hub gap 9 is additionally transported radially.

It is stressed that the magnet bearing according to the invention is not limited to cylindrical forms of the magnets. Other geometric designs of the permanent magnet bearing elements 41 and 42 are possible.

Reference Numerals List

1 Tubular hollow body
2 Stabilizer housing
3 Pump housing
4 Mounting
5 Delivery element
6 Elbow
6' Elbow
7 Fluid guide unit
7' Fluid guide unit
8 Rotor gap
9 Hub gap
10 Flow guide element
11 Cable muff
11a Cable
12 Axial stabilizer
31 Motor stator
32 Motor rotor
41 Permanent magnet bearing element
42 Permanent magnet bearing element
43 Positioning sensor
44
45
51
52 Rotor hub
53 Rotor blading
60 Pressure sensor
61 Flow sensor
62 Aortic cannula
63 Connection element
72 Fluid stator blading
72' Fluid stator blading
73 Hub
74 Support
75 Mounting
76 Hub cap
722 End face
723 Rib
724 Rib
725 Projection
726 Bore 80 Conical rotor
81 Conical guide unit

What is claimed is:

1. A delivery device for a single or multiphase fluid, comprising:
   a tubular body for axially guiding the fluid;
   a motor stator arranged outside the tubular body;
   a delivery element arranged within the tubular body and comprising a motor rotor;
   a rotor gap formed between the delivery element and the hollow body for allowing the fluid to pass through;
   mounting arrangements fixedly disposed in axial direction on each side of the delivery element within the tubular body;
   hub gaps formed between the delivery element and the fixedly disposed mounting arrangement;
   first permanent magnet bearing elements disposed in the mounting arrangement;
   second permanent magnet bearing elements disposed in the delivery element; wherein the first and the second permanent magnet bearing elements functionally work together and are magnetized in axial direction and have opposite polarity;
   position sensors associated with each of the first permanent magnet bearing elements;
   a stabilizer disposed around the hollow body;
   wherein the delivery element is arranged without contacting the mounting elements by means of the first and second permanent magnetic bearing elements, the delivery element is rotatable by the motor stator; and
   wherein the sensors and the stabilizer are utilized for determining the position and possible correction of the position of the delivery element.

2. The device according to claim 1, further comprising at least one pressure sensor disposed in the mounting arrangement and a flow sensor arranged on the hollow body.

3. The device according to claim 1, wherein the first and the second permanent magnet bearing elements include flow guide elements disposed in the mounting arrangements.

4. The device according to claim 1, wherein the mounting elements are formed as fluid guides having a plurality of blades.

5. The device according to claim 1, wherein the mounting elements include end faces facing the delivery element and wherein the end faces include a means for removing fluid from the hub gap.

6. The device according to claim 5, wherein the means is one of a rib, a blade, a groove, a protuberance, an eccentrically arranged projection.

7. The device according to claim 1, wherein the delivery element includes end faces which include means for removing fluid from the hub gap.

8. The device according to claim 7, wherein the means is one of a rib, a blade, a groove, a protuberance, an eccentrically arranged projection.

9. The device according to claim 1, wherein at least one of the mounting elements includes an axially extending bore.

10. The device according to claim 1, wherein the delivery element includes a rotor hub comprising at least one rotor blade.

11. The device according to claim 10, wherein the rotor hub includes two rotor blades, axially spaced apart.

12. The device according to claim 10, wherein the mounting elements comprise hubs including hub caps, the hubs are arranged facing away from the delivery element and wherein the hubs and the rotor hub are cylindrical.

13. The device according to claim 1, wherein the delivery element and fluid guide units, are formed conically, having a larger diameter in flow direction.

* * * * *

UNITED STATES PATENT AND TRADEMARK OFFICE
CERTIFICATE OF CORRECTION

PATENT NO.      : 6,742,999 B1                                                        Page 1 of 1
DATED           : June 1, 2004
INVENTOR(S)     : Peter Nüsser et al.

It is certified that error appears in the above-identified patent and that said Letters Patent is hereby corrected as shown below:

Title page,
Item [75], add Johan K. Fremerey as a fourth inventor.
The inventors listed should be: Peter Nüsser, Johannes Müller, Hans-Erhard Peters, Johan K. Fremerey.
Item [30], Foreign Application Priority Data should be:

-- Apr. 20, 1999 (DE)...............................................199 18 841
   Sep. 18, 1999 (DE)..............................................199 44 863.9 --

Signed and Sealed this

Seventh Day of September, 2004

JON W. DUDAS
*Director of the United States Patent and Trademark Office*